United States Patent [19]

Klopping

[11] 4,060,624

[45] Nov. 29, 1977

[54] CONTROLLING FUNGAL CROP DISEASES WITH MIXTURES OF METHYL 2-BENZIMIDAZOLECARBAMATE AND CERTAIN SPECIFIC FUNGICIDES

[75] Inventor: Hein Louis Klopping, Wilmington, Del.

[73] Assignee: E. I. Du Pont de Nemours and Company, Wilmington, Del.

[21] Appl. No.: 676,142

[22] Filed: Apr. 12, 1976

Related U.S. Application Data

[63] Continuation of Ser. No. 486,086, July 5, 1974, abandoned, which is a continuation-in-part of Ser. No. 434,556, Jan. 18, 1974, abandoned, which is a continuation-in-part of Ser. No. 260,196, June 6, 1972, abandoned, which is a continuation-in-part of Ser. No. 861,791, Sept. 29, 1969, abandoned, which is a continuation-in-part of Ser. No. 727,036, May 6, 1968, abandoned, which is a continuation-in-part of Ser. No. 629,914, April, 1967, abandoned.

[51] Int. Cl.² .................. A01N 9/22; A01N 9/12
[52] U.S. Cl. .................. 424/273 R; 424/286; 424/328
[58] Field of Search .......... 424/273, 286, 289, 328

[56] References Cited

U.S. PATENT DOCUMENTS

| 2,933,502 | 4/1960 | Klopping | 260/299 |
|---|---|---|---|
| 2,933,504 | 4/1960 | Klopping | 260/309.2 |

Primary Examiner—V. D. Turner

[57] ABSTRACT

Mixtures of methyl 2-benzimidazolecarbamate with tetramethylthiuramdisulfide, tetraethylthiuramdisulfide or zinc dimethyldithiocarbamate provide good control of many plant pathogenic fungi. These mixtures also prevent the selective multiplication of resistant strains of fungi in populations of fungi which are normally susceptible to control by methyl 2-benzimidazolecarbamate.

5 Claims, No Drawings

CONTROLLING FUNGAL CROP DISEASES WITH MIXTURES OF METHYL 2-BENZIMIDAZOLECARBAMATE AND CERTAIN SPECIFIC FUNGICIDES

CROSS-REFERENCE TO RELATED APPLICATIONS

This application is a continuation of application Ser. No. 486,086, filed July 5, 1974, now abandoned which is a continuation-in-part of my copending application Ser. No. 434,556 filed Jan. 18, 1974, now abandoned which is a continuation-in-part of my copending application Ser. No. 260,196, filed June 6, 1972, now abandoned, which is a continuation-in-part of abandoned application Ser. No. 861,791, filed Sept. 29, 1969, which is a continuation-in-part of abandoned application Ser. No. 727,036, filed May 6, 1968, which is a continuation-in-part of abandoned application Ser. No. 629,914, filed Apr. 11, 1967.

BACKGROUND OF THE INVENTION

Fungus populations of the genus Cercospora which cause diseases of celery, peanuts, sugar beets and bananas; of the genus Botrytis which cause diseases of grapes, tomatoes, lettuce and strawberries; and of the family Erysiphaceae which attack numerous plants occasionally contain minor segments of particular genetic types (strains) which respond to chemicals differently than the major portion of the population. Under common protective regimens, the major portion of the fungus population is controlled but one or more variant strains survive and, in the absence of competition from their kind, become damaging. Once such a situation has developed, it has been frequent practice to search for another fungicide that can be introduced to control the emerged strain. This invention provides mixtures of fungicides that provide control of the normally susceptible fungi without permitting the emergence to a damaging level of resistant fungus strains that are present.

The use of the individual elements of the composition of this invention are known. Loux U.S. Pat. No. 3,010,968 discloses many benzimidazolecarbamates but does not teach or suggest the use of methyl 2-benzimidazolecarbamate (MBC) as a foliar fungicide. The use of MBC as a foliar fungicide was first taught in Klopping, U.S. Pat. No. 3,657,443. The fungicidal use of tetramethylthiuramdisulfide, tetraethylthiuramdisulfide and zinc dimethyldithiocarbamate is taught in Donald E. H. Frear, *Chemistry of the Pesticides,* D. Van Nostrand Co., Third Ed., 1955, pages 294–300. However, there has been no suggestion of the uses of combinations of these fungicides to prevent emergence of tolerant strains within populations of normally susceptible fungi.

SUMMARY OF THE INVENTION

Compositions of methyl 2-benzimidazolecarbamate (MBC) with one or more of tetramethylthiuramdisulfide, tetraethylthiuramdisulfide or zinc dimethyldithiocarbamate provide protection for plants against plant pathogenic fungi and prevent the emergence of tolerant strains within populations of normally susceptible plant pathogenic fungi.

The compositions of this invention contain one part of MBC to from 1 to 20, preferably 1 to 10 parts of the tetramethylthiuramdisulfide, tetraethylthiuramdisulfide or zinc dimethyldithiocarbamate. Of the compositions of this invention, combinations of MBC and tetraethylthiuramdisulfide are preferred.

DESCRIPTION OF THE PREFERRED EMBODIMENTS

Methyl 2-benzimidazolecarbamate can be prepared by any of a variety of methods known in the art. Loux, U.S. Pat. No. 3,010,968, discloses that the reaction of o-phenylenediamine and methyl 2-methylthiopseudourea carboxylate produces methyl 2-benzimidazolecarbamate. This fungicide is most effective when used in the form of particles ground to less than 5 microns in diameter.

Tetramethylthiuramdisulfide, tetraethylthiuramdisulfide and zinc dimethyldithiocarbamate are well-known chemicals and methods in the art can be employed for their preparation.

The preferred rates of application for the mixtures of this invention to foliage, stems, and/or fruit of living plants range from 100 to 5,000 ppm of total active ingredient in the spray or dip fluid, or 0.5 to 5 kilos of active ingredient per hectare per application. More preferred rates are in the range of 200 to 2,500 ppm or 0.25 to 2.5 kilos per hectare. The most preferred rates are in the range of 500 to 2,000 ppm or 0.5 to 2 kilos per hectare. Applications may be made from 1 to 10 or more times per growing season.

The proper choice of ratios, rates and numbers of applications will vary depending on the host and environmental conditions. Those skilled in the art of protecting plants from disease will readily make a proper choice.

The fungi against which the mixtures of this invention are particularly effective are: *Cercospora apii,* which causes early blight of celery; *Cercospora arachidicola,* which causes leaf spot of peanuts; *Cercospora beticola,* which causes leaf spot of sugar beets, *Cercospora musae,* which causes Sigatoka disease of banana, *Botrytis cinerea,* which causes gray mold of grapes, tomatoes, lettuce and strawberries; and powdery mildew fungi such as *Erysiphe cichoracearum* on cucurbits; *Sphaerotheca humuli* on roses; *Uncinula necator* on grapes; *Erysiphe graminis* on cereals; and *Podosphaera leucotricha* on apples.

The mixtures of this invention can be formulated as wettable powders, thixotropic suspensions, liquids, granules or dusts by the methods well-known to those experienced in the art of formulation.

Specific examples of the useful compositions as well as the effective methods are set forth below to aid in the understanding of this invention. All proportions are by weight unless otherwise indicated. All particle sizes can be determined by methods disclosed in U.S. Pat. No. 3,657,443 or the references shown therein.

EXAMPLE 1

|  | Percent |
| --- | --- |
| methyl 2-benzimidazolecarbamate | 15.0 |
| tetraethylthiuramdisulfide | 60.0 |
| sucrose | 20.5 |
| methylcellulose | 1.0 |
| sodium alkylnaphthalenesulfonate | 1.0 |
| calcium ligninsulfonate | 2.5 |

The methyl 2-benzimidazolecarbamate is hammer-milled in a Mikro-Pulverizer through a screen having openings of 0.02 inch in diameter. One half of this material is then air-milled twice. The methyl 2-benzimidazolecarbamate is then blended with the other ingredients and the whole is hammer-milled to a particle size essentially less than 50 microns for all components. The resulting wettable powder is added to water to provide a suspension containing a total of 1,500 ppm of the two active components. This suspension is sprayed to run-off on the grapevines in a section of a vineyard at intervals through several growing seasons.

The treated vines remain healthy and yield well during the entire period. Similar untreated vines in an adjacent section are damaged and the yield reduced each season by *Botrytis cinerea* (causing gray mold disease) and *Uncinula necator* (causing powdery mildew). Vines in still another section of the vineyard sprayed with methyl 2-benzimidazolecarbamate alone are free of the diseases during the first years but by the end of the period have significant amounts of both.

EXAMPLE 2

|  | Percent |
| --- | --- |
| methyl 2-benzimidazolecarbamate | 35.0 |
| tetramethylthiuramdisulfide | 35.0 |
| polyethylene oxide adduct of dodecylphenyl | 2.5 |
| methylcellulose (low viscosity) | 0.3 |
| synthetic fine silica | 27.2 |

All components are blended, hammer-milled and then air-milled until the active ingredients are largely reduced to particles of 2 microns or smaller. A section of a celery field in Florida is sprayed weekly with a water suspension of the formulated material containing a total of 1000 ppm of the two active ingredients. This program is repeated on a number of successive celery crops grown on the same soil. All crops remain free of disease and yield well. A similar area in the same field left untreated exhibits only celery plants seriously damaged by the fungus *Cercospora apii*. A third area treated only with methyl 2-benzimidazolecarbamate at the same total fungicide rate remains free of disease during the first crop but contains substantial amounts of *Cercospora apii* by the end of the test period.

EXAMPLE 3

|  | Percent |
| --- | --- |
| methyl 2-benzimidazolecarbamate | 10 |
| zinc dimethyldithiocarbamate | 60 |
| kaolinite clay | 30 |

The ingredients are blended and air-milled sufficiently to reduce 40% of the active ingredients (by weight) to particles of 2 microns or less. This dust concentrate is then blended with talc to provide a dust containing 5% total active ingredient.

The diluted dust is applied weekly to a section of a peanut field in Georgia at the rate of 30 kg per hectare. The same treatment is applied to peanuts growing on the same plot over several successive years. During the entire period, the peanuts treated in this manner remain free of disease and yield well. Peanuts on a similar and adjacent area left untreated are seriously damaged each year by *Cercospora arachidicola*. Still a third area treated with only methyl 2-benzimidazolecarbamate alone at the same total fungicide rate is free of disease for the first years of the test but later shows substantial amounts of fungus growth.

EXAMPLE 4

|  | Percent |
| --- | --- |
| dust concentrate of Example 3 | 7.0 |
| polyethylene glycol 6000 | 13.0 |
| synthetic fine silica | 15.0 |
| talc | 65.0 |

The ingredients are hammer-milled through a coarse screen to provide a 4.9% active dust suitable for application by air. This is applied weekly at the rate of 20 kg per hectare to a portion of a sugar beet field. This program is repeated on the same area for several years. Over the entire period, the treated sugar beets remain free of disease. On the other hand, sugar beets in another portion of the same field left untreated are seriously damaged and reduced in yield every year by the fungus *Cercospora beticola*. In a third area of the same field, only methyl 2-benzimidazolecarbamate is applied at the same total rate and in the same manner. This area is free of disease for the first years but later shows attack by the fungus.

EXAMPLE 5

|  | Percent |
| --- | --- |
| methyl 2-benzimidazolecarbamate | 2.0 |
| tetraethylthiuramdisulfide | 18.0 |
| paraffinic spray oil | 75.0 |
| polyoxyethylene sorbitol hexaoleate | 2.5 |
| polyoxyethylene sorbitol oleate | 2.5 |

The ingredients are blended and sand-ground until the active components have been reduced to a particle size essentially below 3 microns. The resulting suspension can be emulsified into water.

The formulation is added to water to provide an emulsion/suspension containing 5% total active. The resulting dilution is applied at the rate of 40 kg per hectare to a portion of a banana plantation at intervals of 21 days. The program is maintained for a period of several years. During the entire period of the test the treated banana plants remain healthy and vigorous. Banana plants in a similar but untreated portion of the same plantation are attacked and heavily damaged by the fungus *Cercospora musae*. A third portion of the same plantation is treated in the same manner with only methyl 2-benzimidazolecarbamate at the same total active rate. For a considerable period this area remains free of disease but by the end of the demonstration period shows the results of the multiplication of a resistant strain of the fungus.

I claim:

1. A fungicidal composition comprising a fungicidally effective amount of a mixture of methyl 2-benzimidazolecarbamate and an additive selected from the group consisting of tetramethylthiuramdisulfide, tetraethylthiuramdisulfide and zinc dimethyldithiocarbamate, the ratio of methyl 2-benzimidazolecarbamate to the additive being from 1:1 to 1:20.

2. The composition of claim 1 wherein the ratio of methyl 2-benzimidazolecarbamate to additive is from 1:1 to 1:10.

3. The composition of claim 1 wherein the additive is tetraethylthiuramdisulfide.

4. A method of preventing injury to plants due to fungi consisting essentially of applying to the plants a fungicidally effective amount of the composition of claim 1.

5. A method of preventing injury to plants due to fungi consisting essentially of applying to the plants a fungicidally effective amount of a composition of claim 3.

* * * * *